United States Patent [19]

Cywinski

[11] Patent Number: 5,350,415
[45] Date of Patent: Sep. 27, 1994

[54] DEVICE FOR TROPHIC STIMULATION OF MUSCLES

[76] Inventor: Jozef Cywinski, 35 Hendrickson Ave., Rockville Centre, N.Y. 11570

[21] Appl. No.: 27,887

[22] Filed: Mar. 8, 1993

[51] Int. Cl.$^5$ .............................................. A61N 1/18
[52] U.S. Cl. ..................................... 607/68; 607/48; 607/72
[58] Field of Search ..................... 607/48, 49, 68, 71, 607/72

[56] References Cited

U.S. PATENT DOCUMENTS 4,712,558 12/1987 Kidd et al. ............................ 607/48
5,019,788 5/1991 Fischer et al. ........................ 330/9

Primary Examiner—William E. Kamm
Assistant Examiner—George Manuel
Attorney, Agent, or Firm—Michael I. Kroll

[57] ABSTRACT

A devise for trophic stimulation of muscles is provided. The device contains a pulse generation circuit that mimics the Motor Unit Action Potentials, MUAP's that are naturally generated when muscles are innervated. The invention provides the basic method for synthesizing the requisite waveform and provides the apparatus for the synthesis. Alternative pulse conditioning circuits are provided; one using a step-up transformer and one using pulse voltage multipliers. The resulting apparatus is safe, relatively painless to use and does not depend upon muscle contraction to achieve a therapeutic result.

8 Claims, 5 Drawing Sheets

DEVICE FOR TROPHIC STIMULATION OF MUSCLES

BACKGROUND

The instant invention relates to the medical apparatus and method for electrical neuromuscular stimulation to be used by the general population to obtain so called trophic changes in their muscles, as well as by people requiring medical treatment in order to facilitate therapy in some neurodegenerative diseases, also to prevent disuse atrophy after stroke or spinal injury and to treat and prevent some other musculoskeletal injuries.

PRIOR ART

Neuromuscular stimulation (NMS) or FES (functional electrical stimulation) are known techniques to cause muscles to contract by means of application of electrical current. Many types of electrical muscle stimulators were developed in the past in order to achieve mechanical and/or functional effects of electrically stimulated muscle contractions. A typical muscle stimulator consists of an electrical pulse generator and a multiplicity of stimulating electrode means. The electrodes are placed on the skin and trains of electrical pulses from the pulse generator are applied to them in order to produce a contraction of underlying muscles or groups of muscles. The prior art stimulators as those disclosed by Axelgaard (U.S. Pat. No. 4,326,534) and Hansjurgens and Mionkowski (U.S. Pat. No. 4,598,713) have controls which allow the clinician or a patient to select stimulation parameters which are suited for the intended purpose, namely to achieve effective, painless, and properly timed muscle contractions. Generally, such controls permit the selection of pulse repetition rate (frequency) and pulse intensity (amplitude of electrical current pulse, or its time duration, or both). These stimulators usually also have the means of timing a succession of contraction/relaxation cycles by "time on" and "time off" controls. Some stimulators also permit gradual onsets of contraction by means of a "ramp up" control. The application of such prior art stimulators for the treatment of patients is usually done by medical practitioners.

After placing the electrodes optimally on the patient's skin, the clinician adjusts the intensity, rate, time on, time off, and ramp up parameters to a setting that produces desired contraction. Often the clinician adjusts one or more parameters and continues to observe the effects on the patient until a desired regimen is achieved. Some patients may then take home the simulator to continue to use the same regimen. This requires the patient to remember all settings, which results in uncertainty and inconvenience. Some simulators addressed this issue by having means to insure that none of the settings are disturbed.

More recent simulators, as disclosed by Morawetz and Burdette (U.S. Pat. No. 4,528,984) include program and execute modes to accomplish storage of parameters by using electronic memory. All of these muscle stimulators were designed to be applied for the purpose of achieving muscle contraction and therapeutic or functional benefits derived therefrom. Such contractions are accomplished as a result of applications of bursts of electrical impulses, each burst containing pulses of a predetermined rate, usually in excess of a certain minimum rate to produce so-called "tetanus" type of muscle contraction. If such a stimulation burst causing contraction continues for more than a few seconds, the muscle will begin to painfully fatigue even at low levels of contraction. Therefore, all of the stimulators incorporate means of repetitively interrupting contractions during the relaxation ("time off") periods.

The occurrence of such fast onset of muscle fatigue associated with stimulated tetanus contractions is in sharp contrast with natural voluntary contractions, which, even at moderate levels, can be maintained for several minutes without fatigue and pain. This is because during fused tetanus types of contractions, all stimulated segments of the muscle contract at the same time and continuously sustain such contraction.

Conversely, during a nonstimulated, i.e., voluntary contraction, the entire segments of the muscle, the so-called motor units, work intermittently and asynchronously. This means that, at first, only some of the motor units contract, exert force, and then fatigue. The fatigued units subsequently cease to contract and go into a relaxation state. This causes the neural feedback mechanism to quickly recruit other, as yet unfatigued, or already rested motor units to take over and contract in order to maintain continuity of the overall muscle contraction.

Such intermittent action of individual motor units was subjected to many scientific investigations where the electrical potentials corresponding to and present in them during various types of voluntary contractions were recorded and analyzed. Such electrical discharges in individual groups of muscle cells which contract together are called Motor Unit Action Potentials, MUAP. The mean rate of firing in most MUAP's is between 5 and 15 pulses per second, which is far below the stimulation rate necessary to achieve fused and forceful contraction of a muscle. When muscles are electrically stimulated with impulses at such a low repetition rate, they apparently do not fatigue. Unfortunately, they do not maintain smooth contraction either. However, such muscle stimulation at a low rate close to the mean rate of the MUAP's has resulted in slow and progressive trophic transformations of the stimulated muscles.

In the review of research reports, Pette and Vrbova (Muscle and Nerve, 8:676,1985) indicated that some of the properties of skeletal muscle fibers can be changed by means of electrical stimulation without the emphasis on mechanical contractions. In fact, a trophic transformation of fast-fatiguing muscle fibers into slow twitching and fatigue-resistant muscle fibers was accomplished by means of a prolonged and constant low-frequency (10 Hz) stimulation which is known not to result in the forceful tetanus-type muscle contraction. In was further discovered that the induced trophic changes in muscle fibers are stimulation rate specific and are not necessarily related to the mechanical contraction of the muscle itself. In the innervation experiments on animals, these changes were further discovered to be dependent on the MUAP activity pattern of the respective motor neurons.

The invention disclosed in 1987 by Kidd, Mather and Cywinski (U.S. Pat. No. 4,712,558) is based on the fact that the occurrence in nature of individual motor units, the so-called MUAP's, determine not only the short term effect, namely muscle mechanical contractions, but also long term effect, namely the trophic changes in mechanical and metabolic properties of the group of muscle cells that these motor unit neurons supply. Furthermore, according to the aforementioned invention, these specific MUAP firing patterns were recorded from live motor nerves under conditions such as fatigue after endurance training exercises. There patterns are nature's way of coping with demands placed on exercised muscle and they produce a natural adaptation of the muscle to perform work at a higher endurance level.

The above prior art invention disclosed the use of these recorded MUAP patterns for stimulation of muscles in order to rapidly and effectively induce functional and structural trophic changes in the muscle. Accordingly, the natural firing pattern of MUAP sequences were recorded from motor neurons, by electronic means, and stored electronically in the memory of the apparatus described in the above referenced invention. These pulse sequences from the apparatus memory were subsequently conditioned and used for obtaining the desired trophic effects in the stimulated muscles. While such a method for muscle stimulation is most likely to be effective to produce desirable trophic changes in a stimulated muscle, from the practical point of view, however, it is not practical, cost-effective, and not easy to use.

There is still an unfulfilled need for a small, simple neuromuscular stimulator device, suitable for individual use, that is capable of effectively accomplishing desirable trophic changes of muscle contractile properties. Of pivotal interest for therapy and prevention of certain neuromuscular diseases and injuries is the stimulation of trophic change of muscle contractile properties from fast fatiguing into slow fatigue resistant types.

SUMMARY

It is, therefore, a primary object of the instant invention to provide a device for trophic stimulation of muscles that emulates the body's natural Motor Unit Action Potentials, or MUAPs, and applies electrical pulses analogous to MUAPs to muscles in order to effectively induce functional and structural trophic changes in the muscle.

Another object is to provide a device for trophic stimulation of muscles that emulates MUAPS by applying an effective predefined set of pulses instead of leaving it to the practitioner to determine the optimum pulse sequence application.

A further object is to provide a device for trophic stimulation of muscles with a visual monitor that allows a user to track the stimulation pulses and provide the count of total pulses delivered during the course of therapy.

Another further object is to provide a device for trophic stimulation of muscles with a control circuit that inhibits generation of stimulation pulses once some predetermined number of pulses have occurred.

A yet further object is to provide a device for trophic stimulation of muscles that is relatively simple and inexpensive to build and is easy and safe to operate.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

DRAWING DESCRIPTION

The figures in the drawings are briefly described as follows:

FIG. 4 is an electronic block diagram of

COMPONENTS

Figure 1:
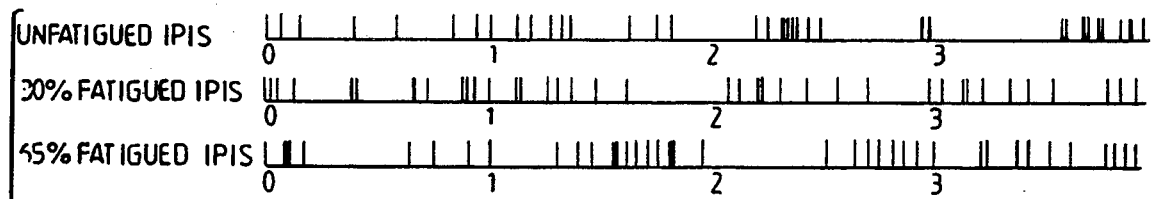
FIG. 1 is an electronic pulse diagram of the Motor Unit Action Potentials (MUAPs) recorded from live experiments under various conditions of muscle fatigue.
Figure 2:
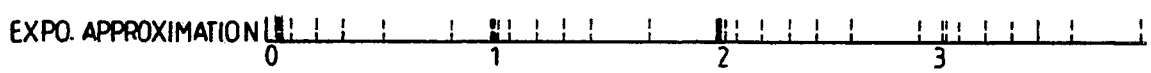
FIG. 2 is an electronic pulse diagram illustrating a synthesized analog of the MUAPs in FIG. 1.

| DRAWING NUMBER | DESCRIPTION |
| --- | --- |
| 1 | Pulse Generator |
| 2 | Pulse Conditioner |
| 3 | Output to Electrodes |
| 4 | Clock Circuit |
| 5, 6, 7, 8 | Oscillator |
| 9 | Mixer |
| 11 | Control and Timing Circuits |
| 14 | Light Emitting Diode(s) |
| 17 | 14-Stage Binary Counter IC |
| 18 | Voltage Controlled Oscillator |
| 19 | Dual Monostable Multivibrator |
| 20 | Potentiometer |
| 21 | Diode |
| 22 | FET Transistor |
| 23 | Step-up Transformer |
| 24 | Bipolar Transistor |
| 25, 26, 27 | FET Transistor |
| 28 | Bipolar Transistor |
| 29, 30 | Decade Counter |

DETAILED DESCRIPTION

The present invention discloses the method and apparatus for inducing lasting trophic changes in muscle contractile properties. This is done by means of the application of electrical stimulation with the special variable-rate sequence of impulses similar to, and patterned after MUAP's occurring in human motor nerves during natural contractions of muscles.

The subject of this invention is an apparatus and method for the electrostimulation of muscles, which electronically synthesizes the stimulus firing patterns to be similar to some of the MUAP rate-sequences and delivers them to patient's muscles by means of transcutaneous electrical simulation techniques. Such a stimulator contains no fixed recording in its memory; i.e. no pulse patterns obtained from live subjects. Conversely, it synthesizes, by means of electronic circuitry, the inter-pulse interval pattern to be similar to that of MUAP. In order to determine the characteristics of the interpulse interval pattern for synthesis, the regularities in seemingly random MUAP sequences were examined. Then measurements were taken on interpulse intervals of MUAP recordings taken during voluntary contractions of hand muscles, as well as those in U.S. Pat. No. 4,712,558 and published elsewhere in the public domain medical literature. A mathematical operation known as sampled predictive running average, was applied to these measurements, and it was discovered that the seemingly random firings of MUAP's are similar in nature to all examples of the recordings, and that they can be approximated by the mix of the following time-domain functions:

1). A continuous low-rate firing activity which can be described mathematically as a delta function continuously pulsing at a slow rate with interpulse intervals (IPI) in a range of approximately 120–200 milliseconds (ms).

2) On this low base rate (described in Point 1) of a continuously repetitive slow pulse activity, there is superimposed a rectangular-like rate modulation with exponential rise and fall, which quickly (T=20 to 40 ms) changes this low base rate into a burst of high rate pulses with short IPI in a range of about 10–20 ms.

3. This decrease in IPI don to a fast rate (described in Point 2) lasts only for about 40 ms, i.e., for approximately three to four pulses during this high rate burst.

4. This high burst rate then declines exponentially into a slower rate with IPI of approximately 60 to 80 ms. Then, after approximately 500 ms, it decreases further do to a base slow rate of 120–200 ms (described in Point 1).

The high rate burst modulation (described in Point 3) as well as the entire cycle of rate changes (described in Points 1–4), has an approximate recurrence period of 1+/−0.2 seconds.

The aforementioned time-domain features of the stimulator pulse generating means to perform in a fashion similar to the above described time sequence pattern. The pulse generating means which produce these timing patterns are then used for the triggering of electrical stimulation to the respective muscles by the electrode means.

Figure 3:
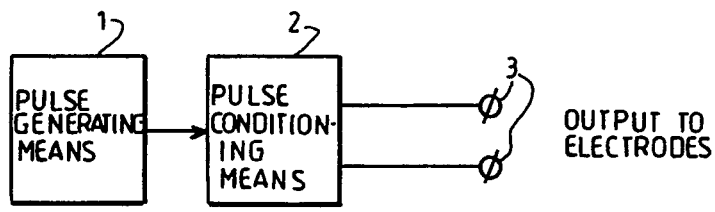
FIG. 3 is a top-level electronic block diagram illustrating the main components of the invention including the pulse generating and pulse conditioning means.

A general block diagram of the entire stimulation system is illustrated in FIG. 3. It comprises the pulse generation means 1 that produce varying pulse interval pattern signals similar in character to those recorded in live experiments as MUAP and described herein. Further, it comprises pulse generation means 2, otherwise known as a stimulator output circuit. These pulse conditioning means are connected by a set of cables to a multiplicity of stimulating electrode means 3. The electrodes are subsequently placed on the skin of patients directly over the treated muscle or over the nerve pathway leading to the respective muscle(s).

Figure 4:
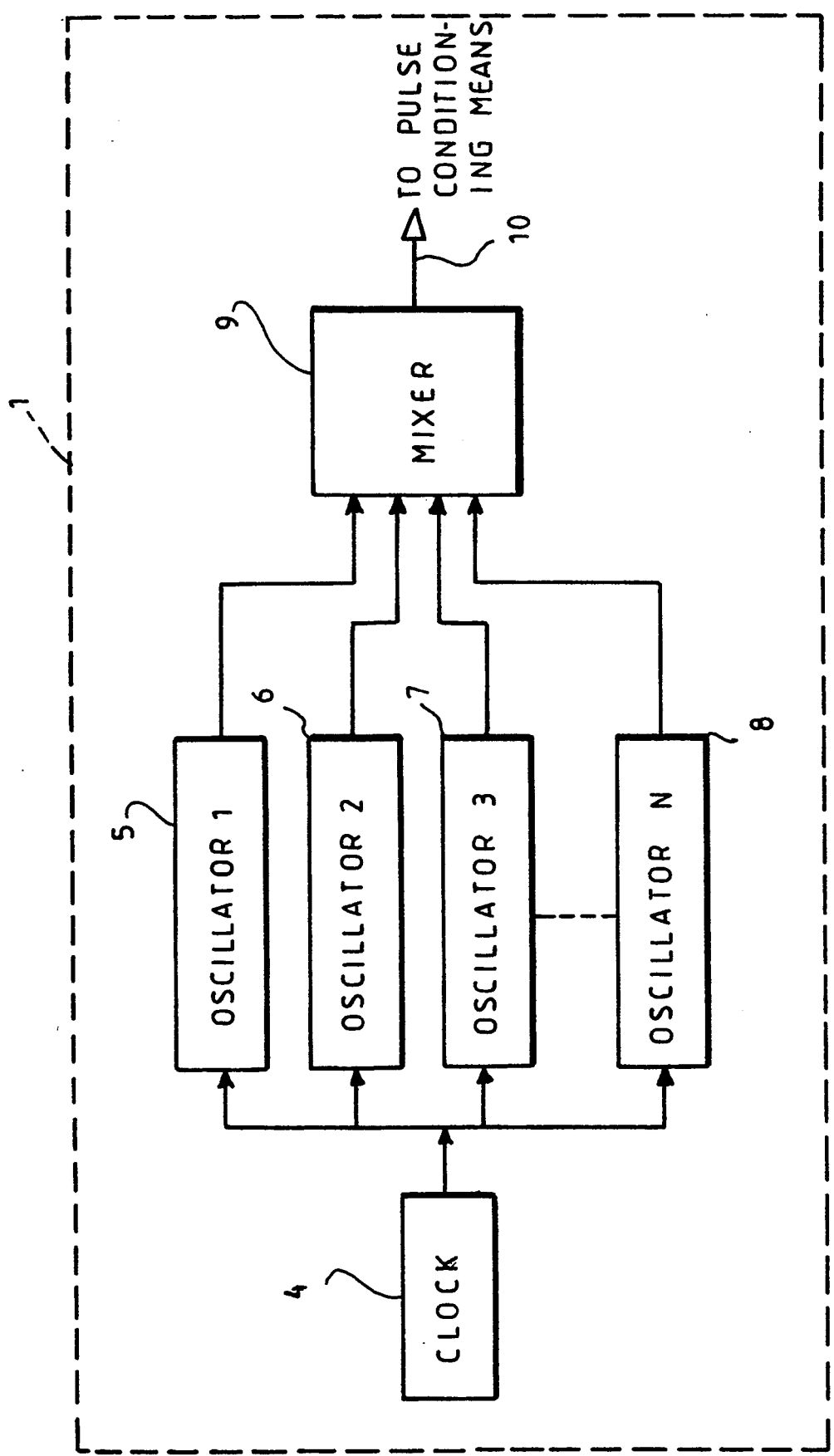

The principal structures of the pulse generation means are show in the block diagram of FIG. 4. There are a multiplicity of electronic oscillators 5,6,7, and 8, working simultaneously and synchronized with each other. The synchronization is assured by the clock component 4. The outputs of the oscillators are coined by an electronic mixing means 9. The waveform at the output 10 of mixing device 9 has a predetermined sequence of interpulse intervals which approximate the natural MUAP time interpulse interval sequence. Therefore, the oscillators 5,6,7 and 8 can be prewired at the factory and they do not require further adjustments when in use.

Figure 5:
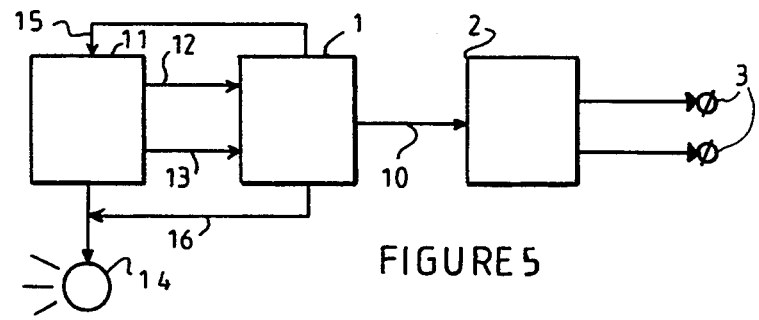
FIG. 5 is an electronic block diagram, similar to FIG. 3, with the addition of a control and timing circuit.

As shown in FIG. 5, the output signals from the pulse generation means 1, and made available at its output 10, are used to trigger the pulse conditioning output circuit 2. The conditioning of pulses is necessary in order to be compatible with the requirements for the stimulation through the skin electrodes 3 to the underlying muscles. The pulse conditioning output circuit is connected to the skin electrode means, which in turn delivers the stimulation signal adequate to override or replace the natural neural signals to the muscles in order to accomplish the desired trophic transformation effects there.

This apparatus for trophic neuromuscular stimulation has no need for user-accessible adjustments except for the strength control (i.e., the amplitude) of stimulating pulses. Due to these pulse timing sequences and due to the device's pulse conditioning design, it is for more comfortable, and less painful, to patients. It causes the desired trophic transformation of muscle in relatively shorter times than older methods, with added patient convenience and simplicity of use.

The general function of this invention is best understood with reference to FIG. 5. The first three basic functional components of the invention are numbered 1,2 and 3 and have been previously described as pulse generating means, pulse conditioning means and electrode means, respectively. Component 11 is the control and timer circuit and the component 14 is the stimulating pulse monitoring display. The control and timer circuit 11 is driven by the clock input 15 coming from the pulse generating means 1. It produces an inhibit signal for the pulse generating means on it output 13. This signal stops the stimulator after a predetermined treatment time. The control and timer circuit 11 also produces a reset signal for the pulse generating means 1 on its output 12. The display monitoring lights are driven by the pulse signals on the input 16 synchronously with each pulse generated by the pulse generating means 1.

Figure 6:
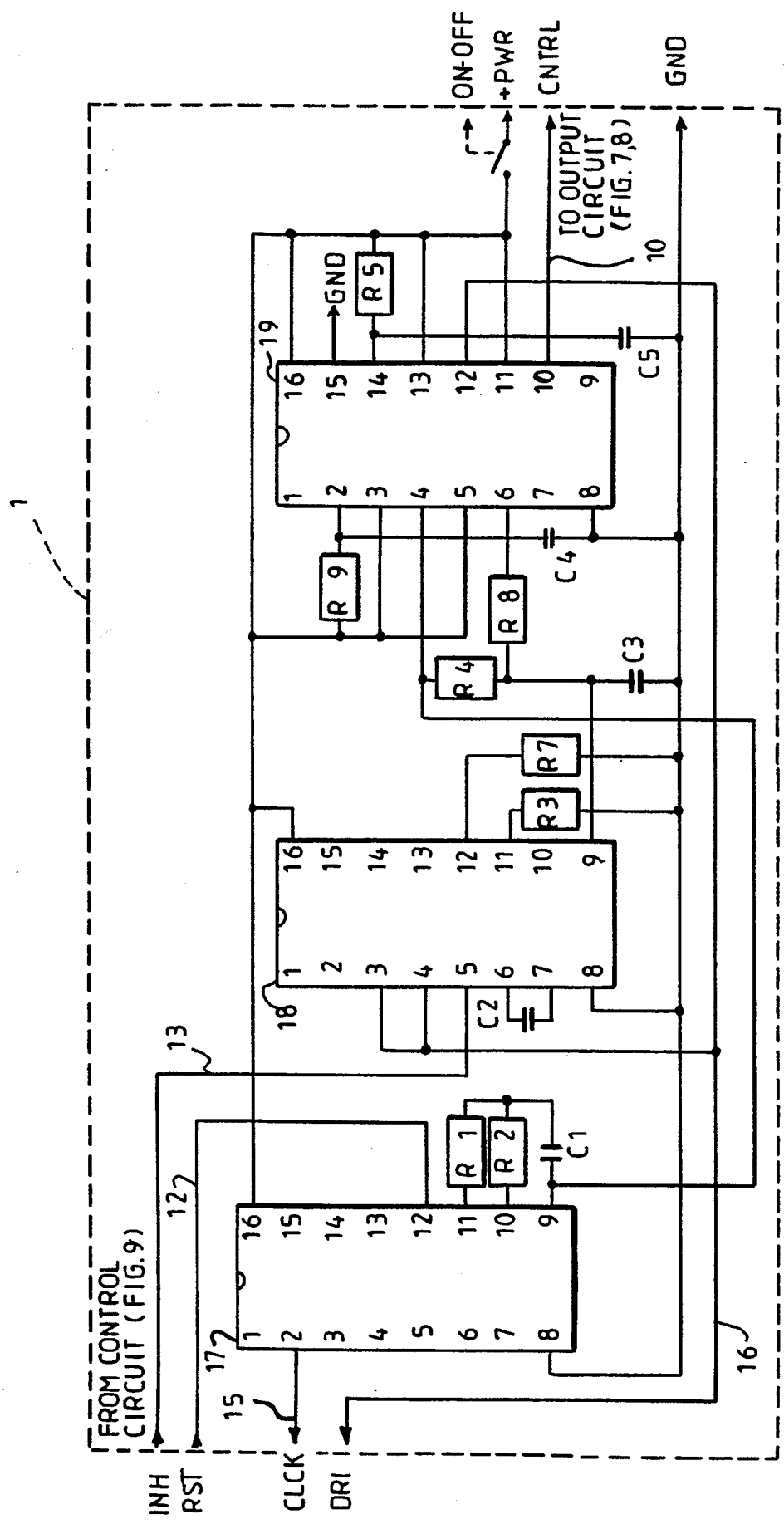
FIG. 6 is a detailed electronic schematic diagram of the pulse generating circuit.

FIG. 6 illustrates the detailed circuit diagram of the pulse generating means 1. This includes a 14-stage binary counter-oscillator integrated circuit 17. This circuit generates clock impulses and also divides the clock frequency by certain powers of the number 2 using those for timing and control functions. The frequency generated by the oscillator within the circuit 17 is fixed and determined only by the time constant of elements C1, R2 and R1 connected to its pins number 9, 10 and 11 respectively. The integrated circuit 18 in the middle of FIG. 6, is a phase-locked-loop voltage controlled oscillator. This circuit generates its o frequency determined by the time constant of elements C2, R3 and R7, and also by the voltage on its input pin 9.

The pulses from the clock oscillator in circuit 17 are fed to the input pin number 9 of this second integrated circuit 18 via the resistor R4. The third integrated circuit 19, is a dual monostable multivibrator. First, it converts the clock waveforth supplied from output pin 9 of the circuit 17 at its input pin 4. The conversion from a 50% duty cycle to another duty cycle is determined by capacitor C4 and resistor R9 connected to pin 2 of circuit 19. The modified duty cycle waveform of the clock frequency present at output pin 4 of monostable multivibrator circuit 19 is fed to input pin 9 of the voltage controlled oscillator 18 via resistor R8. This R8 resistor, together with resistor R4 and capacitor C3 constitute a waveform forming and mixing network presenting its resulting voltage waveform to input pin 9 of the voltage controlled oscillator 18, which determines its firing frequency.

The firing time pattern at the output pins 3 and 4 of oscillator 18 is a compounded result of the instantaneous voltage waveform appearing on its input pin 9 and its time constants as predetermined by the elements C2, R3 and R7. These elements also determine the upper and lower boundaries of the firing rate of circuit 18. The voltage waveform from the output pins 3 and 4 of circuit 18 is fed to the input pin 12 of monostable multivibrator circuit 19. This monostable circuit determines the time duration for each pulse which is predetermined by the time constant of its resistor R5 and capacitor C5. The resulting output waveform appears at pin 10 of integrated circuit 19.

The proper selection of resistive and capacitive elements, namely C1, R1, C2, R2, C3, R3, C4, R4, R7, R8 and R9, determine all time constants of the pulse generating means circuit 1. As illustrated in FIG. 6, the resulting waveform at output 10 of monostable multivibrator 19, is made to represent the timing sequence of an interpulse interval pattern approximating naturally occurring Motor Unit Action Potentials (MUAP's).

In order to accomplish effective stimulation, these pulse timing sequences representing MUAP's, from output 10 on FIG. 6, are applied to the input of pulse conditioning means 2 (see FIGS. 3 and 5). The detailed circuit diagram of the two variants of the examples of detailed embodiments of pulse conditioners are shown in FIGS. 7 and 8.

Figure 7:
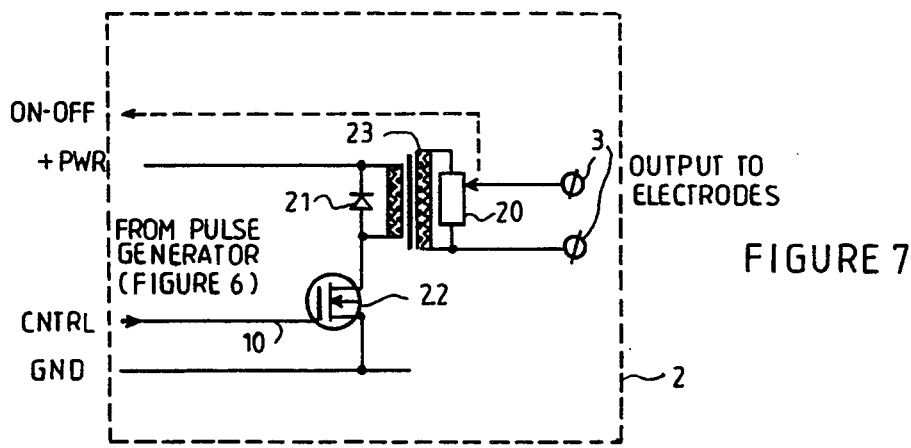
FIG. 7 is a detailed electronic schematic diagram illustrating a first embodiment of the output components of the pulse conditioning circuit, showing the use of a step-up transformer to power the electrodes.

A pulse conditioning means 2 using a transformer output stage is shown in FIG. 7. Here, the step-up transformer 23 with a turns ratio of approximately 1:5, is driven by a power FET transistor 22 which, in turn, is controlled by the sequence of pulses coming to input line 10 from the pulse generating means 2. Diode 21 is in the primary winding of transformer 23 to prevent overvoltage spikes. The secondary winding of transformer 23 is connected to potentiometer 20 which controls the amplitude of the pulses going to the electrode output 3. While this is a relatively simple circuit, its performance and applicability depend greatly on the care and quality in the design of the transformer and its matching to the characteristic load of the electrodes placed over the skin on the muscles.

Figure 8:
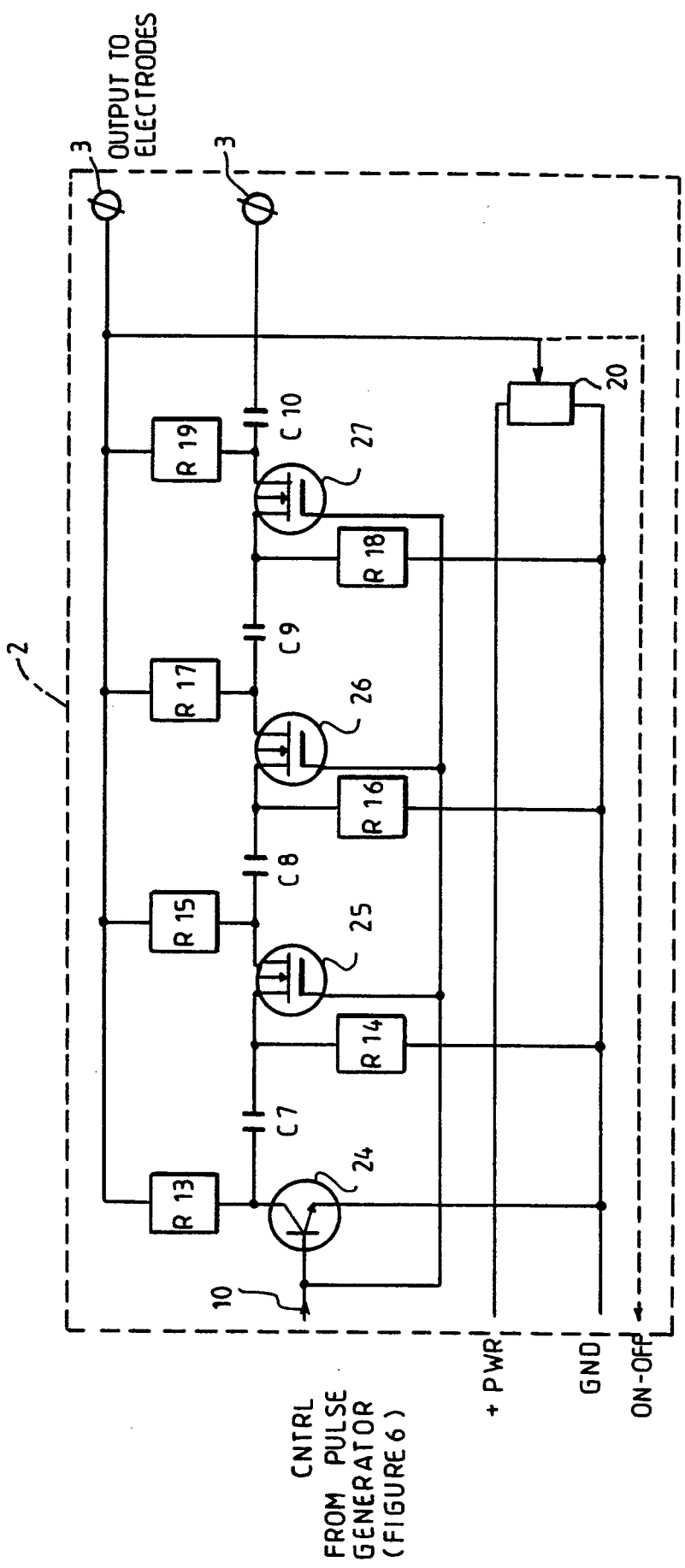
FIG. 8 is a detailed electronic schematic diagram illustrating a second embodiment of the output components of the pulse conditioning circuit, showing the use of a voltage multiplier to power the electrodes.

The second means of pulse conditioning means 2 is shown in FIG. 8. This is a transformerless design using the pulse voltage multiplier principle to achieve proper stimulus voltage and current in the electrode circuit 3. Here, the transistors 24, 25, 26 and 27 discharge the chain of four capacitors C7, C8, C9 and C10 connected through them in series. This discharge takes place through the electrode circuit 3 during the duration of each pulse at the input line 10. The capacitors are subsequently recharged during interpulse intervals while drawing current in parallel from the power supply line through the resistors R13, R14, R15, R16, R17, R18 and R19. This series-parallel arrangement of capacitors gives the pulses conditioning means 2 the effective multiplication of the output voltage by a factor of 5. The output pulse voltage presented at electrodes 3 is controlled by the potentiometer 20 which sets the power supply voltage to the voltage multiplying circuitry. As before, the performance of this circuit depends on the careful matching of its characteristics to the load conditions between electrodes 3.

Figure 9:
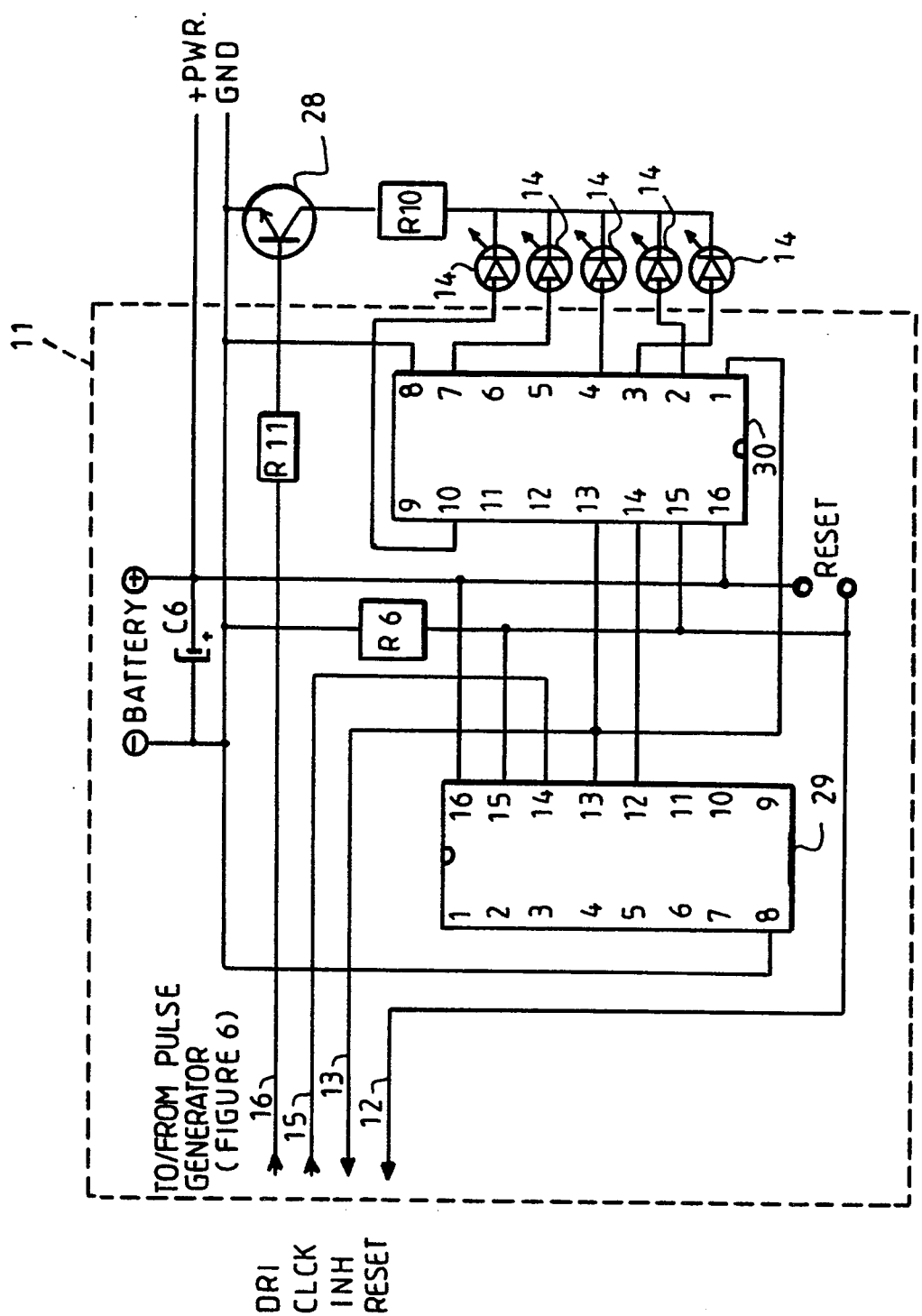
FIG. 9 is a detailed schematic diagram illustrating the control and timing circuits.

FIG. 9 best illustrates the control and timing circuitry. It comprises two integrated circuits and five light emitting diodes 14. The decade counters are connected in series and serve a as time measuring device. They divide the clock pulses on input line 15 by a factor of 50 and after each 10 pulses of the clock activate subsequent Light Emitting Diodes. The diodes are driven on the opposite side by a driver transistor 28 which is switched on during each pulse of the input line 16. After counting to the total number of 50 clock pulses, decade counter 27 issues an inhibit signal on line 13 which stops the pulse generating means 2 and also stops the entire stimulator treatment until the next manual reset activation. While these timing functions are not essential for the course of stimulation treatment, they provide convenience for visual monitoring and for the automated dosage of the treatment time.

While certain novel features of this invention have been shown and described and are pointed out in the annexed claims, it will be understood that various omissions, substitutions and changes in the forms and the details of the device illustrated and in its operation can be made by those skilled in the art without departing from the spirit of the invention.

I hereby claim:

1. A device for trophic stimulation of muscles comprising:
   a. a pulse generator for generating electro-optical emitter signals that are an analog of Motor Unit Action Potentials that naturally occur in muscle contractions;
   b. a pulse conditioner for taking the output of said pulse generator and producing signals that are appropriate for the electrical simulation of muscles;
   c. at least two electrodes for applying the electrical output of said pulse conditioner to skin overlying the muscles to be simulated;
   d. a continuous low-rate firing activity that can be described mathematically as a delta function continuously pulsing at a slow base rate with interpulse intervals in a range of approximately 120 to 200 milliseconds;
   e. a superimposed rectangular-like rate modulation with exponential rise and fall, with T=20 to 40 milliseconds, changes said slow base rate into a burst of high rate pulses with short interpulse intervals in a range of about 10 to 20 milliseconds; wherein said high burst rate then declines exponentially into a slower rate with interpulse intervals of approximately 60 to 80 milliseconds, and, after approximately 500 milliseconds, decreases further to said slow rate of 120 to 200 milliseconds; and wherein said high rate burst modulation, as well as the entire cycle of rate changes described herein has an approximate recurrent period of 1 plus or minus 0.2 seconds; and
   f) a transformerless design using pulse voltage multiplication, wherein said pulse voltage multiplier circuit comprises cascaded transistors driving capacitors connected in series such that when said transistors are fired on, the output voltage is the sum of all the voltages stored in said capacitors.

2. A device for trophic stimulation of muscles, as recited in claim 1, wherein said pulse generator comprises a multiplicity of electronic oscillators working simultaneously and synchronized with each other; and an electronic mixing device whereby the outputs of said oscillators are combined.

3. A device for trophic stimulation of muscles, as recited in claim 2, whereby said oscillators can be pre-wired and require no further adjustment since the natural Motor Unit Action Potentials that is emulated comprises a predetermined sequence of interpulse interval sequences.

4. A device for trophic stimulation of muscles, as recited in claim 2, wherein the means for synchronizing said multiplicity of oscillators comprises a clock circuit.

5. A device for trophic stimulation of muscles, as recited in claim 4, wherein said pulse generator further comprises:
   a. a 14-stage binary counter-oscillator to generate clock impulses and divide the clock frequency by powers of 2 using those for timing and function controls;
   b. a phase-locked loop voltage controlled oscillator whose input are said clock pulses;
   c. a first monostable multivibrator that converts the duty cycle of 50% to a duty cycle determined by an associated RC circuit, wherein the modified duty cycle waveform of the clock frequency is input to said voltage controlled oscillator via an RC waveforming network; and,
   d. a second monostable multivibrator whose input is the output of said first monostable multivibrator, wherein said second monostable multivibrator determines the time duration of each pulse as determined by the time constant of an RC circuit, whereby the output of said second monostable multivibrator circuit is the analog of the Motor Unit Action Potentials.

6. A device for trophic stimulation of muscles, as recited in claim 1, wherein a first embodiment of said pulse conditioning means comprises a transformer output stage driven by a field effect transistor that is controlled by the pulses at the output of said pulse generator wherein the amplitude of the output of said pulses delivered to electrode means is controlled by a potentiometer.

7. A device for trophic stimulation of muscles, as recited in claim 1, wherein said control and timing circuit comprise two decade counters and five electro-optical emitters such that said decade counters are devices connected in series hence the clock pulse is separated by a factor of 50, thus, outputs a pulse of light, and wherein at the precise time the electro-optical output reaches a predetermined count which is manually entered by a device operator, an inhibiting signal is delivered from the pulse conditioning means that stops said pulse generator, thus halting stimulator treatment until manual reset occurs by a device operator.

8. A method of applying trophic stimulation to muscle fiber comprising generating and applying to the muscle fibres, or to ovelaying tissue, a stimulus pulse sequence, wherein the pulse sequence is analogous to the Motor Unit Action Potentials occurring naturally in muscle fibers, and comprising a continuous low-rate firing activity that can be described mathematically as a delta function continuously pulsing at a slow base rate with interpulse intervals in a range of approximately 120 to 200 milliseconds, and a superimposed rectangular-like rate modulation with exponential rise and fall, with $T=2$ to 40 milliseconds, changes said slow base rate into a burst of high rate pulses with short interpulse intervals in a range of about 10 to 20 milliseconds, wherein said high burst rate then declines exponentially into a slower rate with interpulse intervals of approximately 60 to 80 milliseconds, and, after aproximately 500 milliseconds, decreases further to said slow rate of 120 to 200 milliseconds, and wherein said high rate burst modulation, as well as the entire cycle of rate changes described herein has an approximate recurrent period of 1 plus or minus 0.2 seconds.

* * * * *